(12) United States Patent
Teshima et al.

(10) Patent No.: US 6,384,289 B2
(45) Date of Patent: May 7, 2002

(54) PROCESS FOR PRODUCTION OF 1,4-BIS (DIFLUOROALKYL)BENZENE DERIVATIVE

(75) Inventors: Seiichi Teshima; Yoshinobu Asako, both of Ibaraki (JP)

(73) Assignee: Nippon Shokubai Co., Ltd., Osaka (JP)

( * ) Notice: Subject to any disclaimer, the term of this patent is extended or adjusted under 35 U.S.C. 154(b) by 0 days.

(21) Appl. No.: 09/758,607

(22) Filed: Jan. 11, 2001

Related U.S. Application Data

(63) Continuation of application No. 09/233,557, filed on Jan. 20, 1999.

(30) Foreign Application Priority Data

Jan. 20, 1998 (JP) ............................................. 10-009135

(51) Int. Cl.[7] ............................................. C07C 22/08
(52) U.S. Cl. ........................ 570/144; 570/161; 570/164; 570/185
(58) Field of Search ................................. 570/127, 144, 570/145, 161, 164, 185; 549/309, 430

(56) References Cited

PUBLICATIONS

Grechkina et al., "Synthesis of 1,1,2,2,9,9,10,10–Octafluoro [2,2]–para–cyclophane", Zhurnal organicheskoi khimii, 1993, 29(10):1999–2001 (English translation attached).
Hasek et al., "The Chemistry of Sulfur Tetrafluoride. II. The Fluorination of Organic Carbonyl Compounds", J.Amer.Chem.Soc., 1960, 82:543–551.
Sondej et al, Journal of Organic Chemistry, vol. 51, #18, pp. 3508–3513 (1986).*

* cited by examiner

*Primary Examiner*—Sreeni Padmanabhan
(74) *Attorney, Agent, or Firm*—Fish & Richardson P.C.

(57) ABSTRACT

A process is provided which allows a 1,4-bis(difluoroalkyl) benzene derivative to be produced inexpensively by a simple procedure without requiring any special facility. This process comprises causing a compound (A) of the following formula (1):

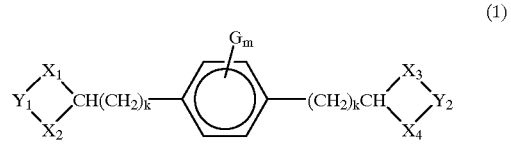

(1)

wherein $X_1$, $X_2$, $X_3$, and $X_4$ independently stand for an oxygen or sulfur atom, $Y_1$ and $Y_2$ independently stand for a group of the formula: $-C_nH_{2n}-$, in which n is 2 or 3, k is an integer in the range of 0 to 4, G stands for a halogen group, an alkyl group, a perfluoroalkyl group, or an alkoxy group, and m is an integer in the range of 0 to 4, to react with a fluorine-containing species, the molar ratio of the fluorine-containing species to compound (A) being in the range of 20–40. The process is carried out in the presence of a bromine-containing compound, which is in an amount of 2 to 3 equivalences to the amount of compound (A), in an organic solvent at −80° C. to 30° C., the final concentration of compound (A) being in the range of 3 to 30% by weight.

4 Claims, No Drawings

PROCESS FOR PRODUCTION OF 1,4-BIS(DIFLUOROALKYL)BENZENE DERIVATIVE

CROSS-REFERENCE TO RELATED APPLICATION

Pursuant to 35 U.S.C. §120, this application is a continuation of, and claims priority from U.S. application No. 09/233,557, filed Jan. 20, 1999.

BACKGROUND OF THE INVENTION

1. Field of the Invention

This invention relates to a process for the production of a novel 1,4-bis(difluoroalkyl)benzene derivative. More particularly, this invention relates to a process which, through a simple and inexpensive procedure relying on the reaction of a compound (A) of the formula (1) with fluorine at a low temperature under a normal pressure, accomplishes the production of a 1,4-bis(difluoroalkyl)benzene derivative which is of the formula (2) and is useful as a raw material for a resin excellent in heat-resistance, chemical-resistance, water-repellency, low dielectric property, and low refractivity.

2. Description of the Related Art 1,4-Bis(difluoromethyl)benzene is used as a raw material for the synthesis of 1,4-bis(bromodifluoromethyl)benzene, which is further used for derivation of per-α-fluoro[2,2]paracyclophane therefrom. This product of derivation allows synthesis of fluorine-substituted Parylene resin (PA-F) which excels in heat-resistance, chemical-resistance, and water-repellency. As methods for producing 1,4-bis(difluoromethyl)benzene, a method which relies on the reaction of terephthal aldehyde with sulfur tetrafluoride ($SF_4$) [J. Am. Chem. Soc., 82, pp. 543–551 (1960)], a method which resorts to the reaction of α,α,α',α'-tetrabromo-p-xylene with antimony trifluoride [RU 2032654, Zn, Org. Khim., 29, pp. 1999-2001 (1993)], and etc. have been known to the art to date.

Of these methods, the former method which uses sulfur tetrafluoride is at a disadvantage in needing such facilities as special reaction vessels made of Hastelloy, a (Ni-Mo type) stainless alloy excellent in corrosion-resistance and, as a consequence, incurring an increase in the cost of production because the sulfur tetrafluoride shows strong toxicity and corrosiveness, costs dearly, and entails such harsh reaction conditions as 150° C. and 8 MPa.

Then, the latter method which uses antimony trifluoride is likewise at a disadvantage in needing special facilities and, as a result, incurring an increase in the cost of production because the reaction involved therein proceeds at such elevated reaction temperatures as 100° to 150° C.

Therefore, a demand for a method which permits 1,4-bis(difluoromethyl)benzene and the derivatives thereof to be produced inexpensively by a simple procedure without requiring any special facility has been still strong.

SUMMARY OF THE INVENTION

This invention, originated in the light of the present situation of prior art mentioned above, has an object to provide a process for the production of a novel 1,4-bis(difluoroalkyl)benzene derivative.

Another object of this invention is to provide a process for producing a 1,4-bis(difluoroalkyl)benzene derivative inexpensively by a simple procedure without requiring any special facility.

The objects mentioned above can be accomplished by a process for the production of a 1,4-bis(difluoroalkyl)benzene derivative of the formula (2):

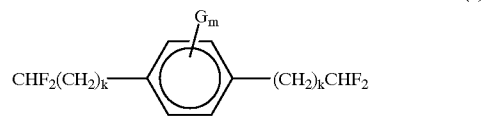

(2)

wherein k is an integer in the range of 0 to 4, G stands for a halogen group, an alkyl group, a perfluoroalkyl group, or an alkoxy group, and m is an integer in the range of 0 to 4, which process comprises causing a compound (A) of the formula (1):

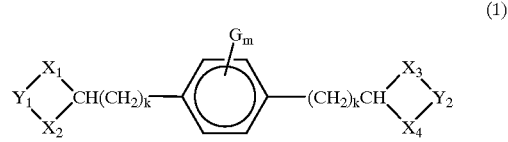

(1)

wherein k, G, and m are as defined above, $X_1$, $X_2$, $X_3$, and $X_4$ independently stand for an oxygen or sulfur atom, and $Y_1$ and $Y_2$ independently stand for a group of the formula: —$C_nH_{2n}$—, in which n is 2 or 3 (hereinafter occasionally referred to simply as "compound (A)"), to react with a fluorine-containing species, the molar ratio of the fluorine-containing species to compound (A) being in the range of 20–40. The process is carried out in the presence of a bromine-containing compound, which is in an amount of 2 to 3 equivalences to the amount of compound (A), in an organic solvent at −80° C. to 30° C., the final concentration of compound (A) being in the range of 3 to 30% by weight.

The above and other objects, features and advantages of the present invention will become clear from the following description of the preferred embodiments.

The process of the present invention permits the omission of such special facilities as have been heretofore needed and also allows 1,4-bis(difluoroalkyl)benzene derivative of the formula (2) to be produced inexpensively as aimed at because the reaction of the compound (A) of the formula (1) with fluorine can be carried out at a low temperature under a normal pressure and also because the fluorine source can be supplied at a relatively low cost.

DETAILED DESCRIPTION OF THE PREFERRED EMBODIMENT(S)

Now, this invention will be described specifically below.

This invention is characterized in producing a 1,4-bis(difluoroalkyl)benzene derivative of the following formula (2) by causing the compound (A) of the following formula (1) to react with fluorine.

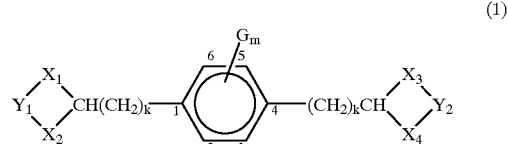

(1)

-continued

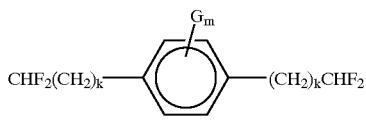
(2)

In the formula (1), $X_1$, $X_2$, $X_3$, and $X_4$ independently stand for an oxygen atom or a sulfur atom, preferably a sulfur atom. In the formula (1), $Y_1$ and $Y_2$ independently stand for a group denoted by the formula: $-C_nH_{2n}-$, in which n is 2 or 3. Though the numerical value of n is suitably selected depending on the reactivity of the compound (A) with fluorine, it is preferably 2. Further, the symbol G in the formulas (1) and (2) represents a halogen group such as a fluoro group, a bromo group, and a chloro group; an alkyl group of one to four carbon atoms such as, for example, a methyl group, an ethyl group, and a propyl group; a perfluoroalkyl group of one to four carbon atoms such as, for example, a trifluoromethyl group and a pentafluoroethyl group; or an alkoxy group of one to four carbon atoms such as, for example, a methoxy group, an ethoxy group, a perfluoromethoxy group, and a perfluoroethoxy group, etc. Among other groups mentioned above, G particularly advantageously represents a halogen group such as a fluoro group, a bromo group, and a chloro group, more preferably a fluoro group or a chloro group, and most preferably a fluoro group. When a plurality of G's are present (namely when m is from 2 to 4), the individual G's may be either the same or different to each other. The symbol m in the formulas (1) and (2) is an integer in the range of 0 to 4, preferably 0, 3 or 4, and more preferably 0 or 4. In this case, the position of linkage of G to a benzene ring is properly selected depending on the reactivity of the compound (A) with fluorine. When m is 2, for example, the linkage is preferred to occur at the (2, 5) position. The numbering used in specifying the position mentioned above is based on the numbers which are assigned to the positions shown in the formula (1) just mentioned above. Furthermore, the symbol k in the formulas (1) and (2) is an integer in the range of 0 to 4, preferably 0 or 1, more preferably 0.

The compound (A) which may be particularly advantageously used in this invention is a compound which is represented by the following formula.

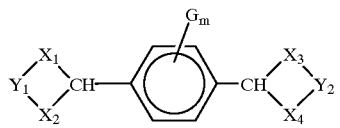

The compound (A) to be used in this invention has no particular restriction, so far as it should be a compound of the formula (1). When k and m in the formula (1) are both 0, for example, it is obtained by causing terephthal aldehyde to react with the compound $(B_1)$ of the following formula (3) and the compound $(B_2)$ of the following formula (4) in accordance with a well-known method. To be more specific, the compound (A) can be prepared efficiently by dissolving terephthal aldehyde in an organic solvent including toluene, adding the compound $(B_1)$ and the compound $(B)_2$ to the resultant solution, heating the mixture, and effecting the reaction aimed at meanwhile expelling the water. For the purpose of improving the yield, the reaction is preferably carried out in the presence of an acid catalyst. As typical examples of the acid catalyst to be used herein, inorganic acids such as hydrochloric acid, sulfuric acid, and nitric acid and organic acids such as oxalic acid, acetic acid, paratoluene sulfonic acid, benzene sulfonic acid, and trifluoroboron ether complex may be cited. Among other acid catalysts cited above, paratoluene sulfonic acid and trifluoroboron ether complex prove particularly advantageous on account of excellent solubility.

In the formulas (3) and (4) mentioned above, the symbols, $X_1$–$X_4$ and $Y_1$ and $Y_2$, have the same meanings as defined in the formula (1) above.

The compound $(B_1)$ and the compound $(B_2)$ to be used in this invention may be either equal or different to each other so long as they should be compounds represented respectively by the formula (3) and the formula (4). As typical examples of the compounds of the formula (3) and the formula (4), 1,2-ethane dithiol, 1,3-propane dithiol, ethylene glycol, 1,3-propane diol, and 2-mercapto ethanol may be cited. Among other compounds mentioned above, 1,2-ethane dithiol and 1,3-propane dithiol may be used particularly advantageously.

The typical examples of the compound (A) wherein in the formula (1), both k and m are 0 according to this invention are as following:

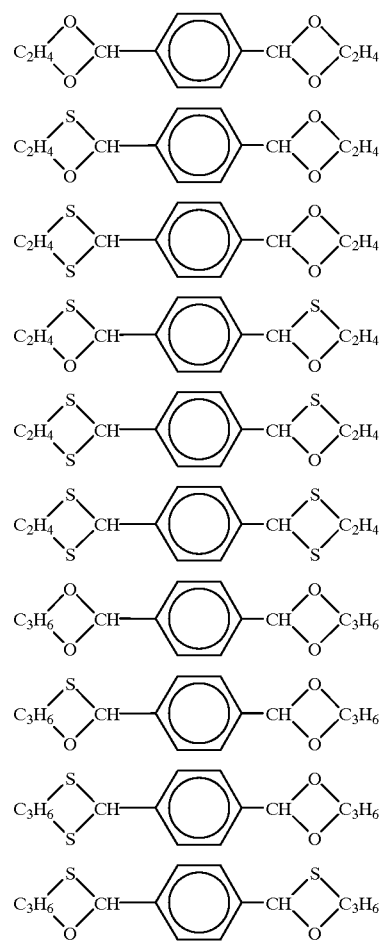

-continued

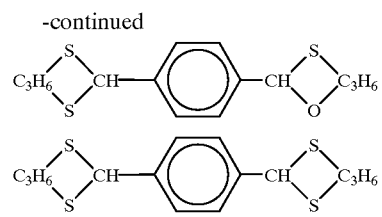

Among these compounds,

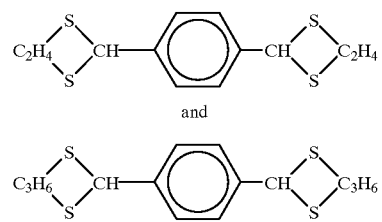

may be preferably used as the compound (A) in this invention.

The term "fluorine", as used herein, includes fluorine molecules ($F_2$), fluorine compounds, and fluorine ions. Of these specific examples of the "fluorine", the fluorine compounds and the fluorine ions may be preferably used as the fluorine according to this invention.

When this invention elects to use a fluorine compound as the "fluorine", it does not need to impose any specific restriction on this fluorine compound. As typical examples of the fluorine compound which may be advantageously usable in this invention, pyridine hydrogen fluoride, ammonium hydrogen fluoride, potassium hydrogen fluoride, hydrofluoric acid, sodium hydrogen fluoride, ammonium fluoride, antimony III fluoride, antimony V fluoride, and cesium fluoride may be cited. Among other fluorine compounds mentioned above, pyridine fluoride, cesium fluoride, and hydrofluoric acid are usable particularly advantageously.

When this invention elects to use a fluorine ion as the "fluorine", it does not need to discriminate particularly the fluorine ions on account of the specific source of fluorine ions to be adopted. They nevertheless may be preferably supplied from the fluorine compound as mentioned above.

This invention does not need to impose any particular restriction on the amount of fluorine but properly selects this amount with consideration for the yield of reaction and the cost of manufacture. For the purpose of enabling the incorporation of fluorine atoms into the compound (A) to proceed efficiently and improving the yield of the product aimed at, the fluorine is preferably present in an excess concentration relative to the compound (A). Specifically, the amount of the fluorine is preferably not less than 4 mols, more preferably in the range of 4 to 100 mols, furthermore preferably in the range of 4 to 40 mols, and most preferably in the range of 4 to 20 mols, per mol of the compound (A). If the amount of fluorine is less than 4 mols, the shortage will be at a disadvantage in preventing the fluorine from being completely incorporated into the compound (A) and consequently lowering the yield of the product aimed at. Conversely, if the amount of fluorine exceeds 100 mols, the excess will be at a disadvantage in bringing no proportionate addition to the yield, only impairing the economy of the reaction, and incurring extra cost in the disposal of the residual fluorine.

Though this invention is allowed to introduce the compound (A) and the fluorine either simultaneously or sequentially, the compound (A) is preferably introduced last of all the reactants in consideration of the yield of the reaction.

The temperature during the reaction of the compound (A) with the fluorine according to the present invention is properly in the range of −100° to 80° C., more preferably in the range of −80° to 30° C., and most preferably in the range of −20° to 25° C., with a view to obviating the necessity for providing a special facility capable of withstanding a high-temperature reaction and preventing the yield from being lowered by the decomposition of reaction reagents. The control of the reaction temperature may be attained by any of various known methods such as, for example, by immersing the reaction solution in a coolant retained at a desired temperature, by flowing into a reaction vessel an inert gas (such as, for example, nitrogen, argon, or helium) cooled in advance with liquid nitrogen, or by bubbling the cooled inert gas through the reaction solution. The reaction time, though variable with the particular kinds of compound (A) and fluorine and the reaction conditions, generally falls within the range of 1 to 24 hours, preferably in the range of 2 to 12 hours.

Though in this invention, the reaction of the compound (A) with the fluorine may be carried out in the absence of a solvent, in the presence of an inorganic solvent, or in the presence of an organic solvent, the reaction may be preferably performed in the presence of an organic solvent because the organic solvent, by dissolving the compound (A) and the fluorine therein, improves the efficiency of the reaction and facilitates the release of heat.

In the above-mentioned embodiment, the reaction of the compound (A) with the fluorine in the presence of an organic solvent may be implemented by adding the compound (A) to an organic solvent containing the fluorine therein, preferably gradually. As used herein, the expression "organic solvent containing the fluorine" means a state in which the fluorine is uniformly dissolved or dispersed in the organic solvent. Specifically, the organic solvent containing the fluorine may be obtained by any of known techniques such as, for example, by adding the fluorine compound mentioned above to the organic solvent which will be specifically described below. In this case, the final concentration of the compound (A) in the organic solvent is required to fall within the range of 1 to 40% by weight, preferably 3 to 30% by weight, in consideration of the yield of the reaction and the cost of production.

Further, in the above-mentioned embodiment, the reaction of the compound (A) with the fluorine in the presence of the organic solvent may be attained by blowing the fluorine such as the hydrogen fluoride gas into the organic solvent containing the compound (A) therein. In this case, the concentration of the compound (A) in the organic solvent is properly in the range of 1 to 40% by weight, preferably 3 to 30% by weight, in consideration of the yield of the reaction and the cost of production. The flow rate of the fluorine gas, though only required to permit the introduction of the fluorine in such an amount as is mentioned above, generally falls within the range of 5 to 200 ml/min., preferably in the range of 10 to 100 ml/min.

The organic solvent which may be used in this invention has no particular restriction, excepting that it be a solvent incapable of being fluorinated. As typical examples of such an organic solvent, aliphatic or aromatic hydrocarbons such as pentane, hexane, cyclohexane, octane, and xylene, halogen-containing aliphatic or aromatic hydrocarbons such as dichloromethane, 1,2-dichloroethane, chloroform, 1,1,2, 2-tetrachloroethane, carbon tetrachloride, trichlorofluoromethane, and chlorotoluene, and diglyme, and tetrahydrofuran may be cited. Among other organic solvents cited above, dichloromethane, chloroform, and 1,2-dichloroethane may be used particularly favorably with a view to enabling the reaction to proceed with high efficiency and thus improving the yield. The organic solvent to be used in this invention may be preferably used in such a dry state as dried with any of such known desiccators as $LiAlH_4$, $CaH_2$, and molecular sieve.

The reaction of the compound (A) with the fluorine according to this invention may be properly carried out in an atmosphere such that the gaseous phase of the reaction system may have a moisture content of not more than 100 volppm, more preferably not more than 50 volppm, and most preferably not more than 10 volppm. If the moisture content exceeds 100 volppm, the excess will be at a disadvantage in degrading the efficiency of the introduction of the fluorine atoms and inducing corrosion of the reaction vessel. With a view to preventing the moisture content from exceeding 100 volppm, therefore, the interior of the reaction vessel, prior to being charged with the solvent containing the fluorine, is preferred to be displaced with an inert gas such as, for example, argon, helium, or nitrogen which has been dried by being passed through liquid nitrogen.

The present invention, for the purpose of further improving the efficiency of the reaction, prefers the reaction of the compound (A) with the fluorine to proceed in the presence of a bromine-containing compound.

In the above-mentioned embodiment, the bromine-containing compound imposes no particular restriction but requires only to contain a bromine atom. It nevertheless is preferred to be a compound possessing as many bromine atoms per molecule as permissible. More preferably, this compound is capable of generating $Br^+$. As typical examples of the compound answering this description, N-bromosuccinimide and 1,3-dibromo-5,5-dimethyl hydantoin may be cited. In this case, the amount of the bromine-containing compound to be present, though it is not particularly limited, is generally in the range of one to three equivalences, preferably in the range of one to two equivalences, based on the amount of the compound (A). The term "equivalent weight" as used herein means the numerical value to be calculated by the following formula.

(Equivalence)=(Number of mols of the bromine-containing compound)×(Number of bromine atoms per molecule of the bromine-containing compound)/[4 (mols)]

The reaction vessel to be used in this invention imposes no particular restriction and requires only to be incapable of being fluorinated. As typical examples of such a reaction vessel, vessels which are made of or coated with glass, polyethylene, polypropylene or a fluorine resin may be cited. Among other coating materials mentioned above, polyethylene, polypropylene, and a fluorine resin may be used particularly advantageously for the purpose of precluding the reaction vessels from the pollution due to the otherwise possible elution of an alkali metal ion and a heavy metal ion.

Then, after the reaction of the compound (A) with the fluorine has been completed, the product aimed at can be isolated from the resultant reaction solution by subjecting the solution to separation or purification by such a known technique as, for example, silica column chromatography, distillation, or recrystallization.

In this case, the yield of the product in the resultant reaction solution is determined by subjecting the reaction solution to gas chromatography furnished with a hydrogen flame ionizing detector. For a fixed content, this method produces a peak strength which is proportionate to the number of carbon atoms of a given sample. For a fixed number of carbon atoms, this method is enabled to accomplish quantitative analysis because the peak strength is proportionate to the amount of the product.

Now, this invention will be described more specifically below with reference to working examples. In the working examples, the yields of the products by relevant reactions were calculated in the same manner as in the embodiment mentioned above. Note that Referential Examples 1–4 and Examples 1–11 and 14–19 are not within the scope of the current invention. Examples 12 and 13, on the other hand, are within the scope of this invention. Examples 1–11 and 14–19 therefore should be deemed as comparative examples.

Referential Example 1

In a three-neck flask, 100 ml in inner volume, made of glass and provided with a stirrer, 6.65 g (50 mmols) of terephthal aldehyde and 50 g of dichloromethane were placed. The reactants, after having added 10 ml (120 mmols) of 1,2-ethane dithiol, were stirred continuously at 25° C. for 20 minutes and, after having subsequently added 10 ml (80 mmols) of a boron trifluoride diethyl ether complex, further stirred continuously at 25° C. for two hours, to form a white precipitate. By filtrating this white precipitate, 10.8 g (75% in yield) of 2,2'-(1,4-phenylene) bis-1,3-dithioran (hereinafter referred to as "Intermediate (1)").

Referential Example 2

In a three-neck flask, 100 ml in inner volume, made of glass and provided with a stirrer and a Dean-Stark trap, 6.65 g (50 mmols) of terephthal aldehyde and 50 g of toluene 50 g were placed. The reactants, after having added 3.4 g (55 mmols) of ethylene glycol and 0.21 g (1 mmol reduced as paratoluene sulfonic acid) of paratoluenesulfonic monohydride, were continuously stirred as refluxed at 110° C. for two hours. The resultant product was separated and refined by silica gel column chromatography, to obtain 8.3 g (75% in yield) of 2,2'-(1,4-phenylene)bis-1,3-dioxoran (hereinafter referred to as "Intermediate (2)").

Referential Example 3

In a three-neck flask, 100 ml in inner volume, made of glass and provided with a stirrer, 4.0 g (30 mmols) of terephthal aldehyde and 30 g of dichloromethane were placed. The reactants, after having added 8.1 g (75 mmols) of 1,3-propane dithiol, were stirred continuously at 25° C. for 20 minutes and, after having subsequently added 6.3 ml (50 mmols) of a boron trifluoride diethyl ether complex, further stirred continuously at 25° C. for two hours, to form a white precipitate. The resultant white precipitate was filtered, to obtain 6.6 g (70% in yield) of 2,2'-(1,4-phenylene) bis-1,3-dithian (hereinafter referred to as "Intermediate (3)").

Referential Example 4

In a three-neck flask, 300 ml in inner volume, made of glass and provided with a stirrer and a Dean-Stark trap, 51.6 g (385 mmols) of terephthal aldehyde, 64.4 g (767 mmols) of ethane dithiol, and 150 ml of toluene were placed. The reactants, after having added 0.037 g (0.19 mmol) of paratoluene sulfonic monohydride, were continuously stirred as refluxed at 110° C. for three hours, with the water generated in consequence of the reaction kept expelled by distillation. The white solid precipitated consequently was separated by filtration and dried, to obtain 100 g (91% in yield) of 2,2'-(1,4-phenylene) bis-1,3-dithioran (hereinafter referred to as "Intermediate (4)").

EXAMPLE 1

In a three-neck flask, 2 liters in inner volume, made of glass and provided with a stirrer, 14.9 g (52 mmols) of 1,3-dibromo-5,5-dimethyl hydantoin (hereinafter abbreviated as "DMH") and 660 g of dichloromethane were placed and thoroughly dissolved by stirring. The three-neck flask, with argon gas (having a moisture content of not more than 1 volppm) continuously flowing through the interior thereof, was immersed in ice water. Then, in the solution in the flask, 25 ml (1060 mmols) of pyridine hydrogen fluoride (HF-Pyridine: produced by Aldrich Corp.; the weight ratio of HF to pyridine: 7 to 3; density 1.2) was added through the medium of a syringe. Further, 7.7 g (27 mmols) of the intermediate (1) prepared in Referential Example 1 was introduced as split into several portions while stirred at 0° C., and continuously stirred at 0° C. for two hours and then made to add 660 g of dichloromethane. The molar amount of HF-Pyridine is about 40 times that of the intermediate (1).

The resultant mixture was distilled to expel the reaction solvent by evaporation and the residue of the distillation was passed through a basic alumina column. When the effluent from the column was analyzed by the GC-MS, it was confirmed to contain therein 4-difluoromethyl benzaldehyde (product 1) and 1,4-bis-(difluoromethyl)benzene (product 2). In the GC analysis which was separately performed, the area ratio of product 1/product 2 was found to be 10/90.

When the reaction mixture obtained in consequence of the preceding operation was distilled under a reduced pressure (50 mmHg, 93° C. to 99° C.), it separated 3.8 g of 1,4-bis(difluoromethyl)benzene (80% in yield).

EXAMPLES 2 to 4

Reactions were performed by following the procedure of Example 1 while changing the temperature of adding the intermediate (1) and the temperature of reaction to the levels shown in Table 1 below and the 1,4-bis(difluoromethyl)benzenes consequently produced were measured for yield. The results of Examples 1 to 4 are summarized in Table 1 below.

TABLE 1

| Example | Temperature (° C.) | Yield (%) |
|---------|---------------------|-----------|
| 1 | 0 | 80 |
| 2 | −80 | 35 |
| 3 | 23 | 60 |
| 4 | 40 | 8 |

From Table 1 given above, it is clearly noted that the 1,4-bis(difluoromethyl)benzene aimed at can be obtained in a high yield by adjusting both the temperature of adding the intermediate (1) and the reaction temperature within the range of −20° to 25° C.

EXAMPLE 5

In a three-neck flask, 200 ml in inner volume, made of glass and provided with a stirrer, 1.49 g (5.2 mmols) of DMH and 66 g of dichloromethane were placed and thoroughly dissolved by stirring. The three-neck flask, with argon gas (having a moisture content of not more than 1 volppm) continuously flowing through the interior thereof, was immersed in ice water. To the solution in the flask, 2.5 ml (106 mmols) of pyridine hydrogen fluoride (HF-Pyridine: produced by Aldrich Corp.; the weight ratio of HF to pyridine: 7 to 3; d 1.2) was added through the medium of a syringe. Then, 0.6 g (2.7 mmols) of the intermediate (2) prepared in Referential Example 2 was introduced as split into several portions while stirred at 0° C. and continuously stirred at 0° C. for two hours and then made to add 66 g of dichloromethane.

The resultant mixture was distilled to expel the reaction solvent by evaporation and the residue of the distillation was passed through a basic alumina column. When the effluent from the column was analyzed by the GC-MS, it was confirmed to contain therein 4-difluoromethyl benzaldehyde (product 1) and 1,4-bis-(difluoromethyl)benzene (product 2). In the GC analysis which was separately performed, the area ratio of product 1/product 2 was found to be 30/70.

EXAMPLE 6

A reaction was performed by following the procedure of Example 5 while using 0.85 g (2.7 mmols) of the intermediate (3) synthesized in Referential Example 3 in place of the intermediate (2).

When the effluent from the column was analyzed by the GC-MS, it was confirmed to contain therein 4-difluoromethyl benzaldehyde (product 1) and 1,4-bis (difluoromethyl)benzene (product 2). In the GC analysis which was separately performed, the area ratio of the product 1/product 2 was found to be 15/85.

EXAMPLE 7

In a three-neck flask, 200 ml in inner volume, made of glass and provided with a stirrer, 1.49 g (5.2 mmols) of DMH and 66 g of dichloromethane were placed and thoroughly dissolved by stirring. The three-neck flask, with argon gas continuously flowing through the interior thereof, was immersed in ice water. To the solution in the flask, 0.77 g (2.7 mmols) of the intermediate (1) prepared in Referential Example 1 was introduced as split into several portions. Then, 2.5 ml (106 mmols) of pyridine hydrogen fluoride (produced by Aldrich Corp.; the weight ratio of HF to pyridine is 7 to 3) was further added as split into several portions through the medium of a syringe, and stirred continuously at 0° C. for two hours and then made to add 66 g of dichloromethane.

The resultant mixture was distilled to expel the reaction solvent by evaporation and the residue of the distillation was passed through a basic alumina column. When the effluent from the column was analyzed by the GC-MS, it was confirmed to contain therein 4-difluoromethyl benzaldehyde (product 1) and 1,4-bis-(difluoromethyl)benzene (product 2). In the GC analysis which was separately performed, the area ratio of product 1/product 2 was found to be 60/40.

EXAMPLE 8

In a three-neck flask, 200 ml in inner volume, made of glass and provided with a stirrer, 1.49 g (5.2 mmols) of DMH and 66 g of dichloromethane were placed and thoroughly dissolved by stirring. The three-neck flask, with argon gas continuously flowing through the interior thereof, was immersed in ice water. To the solution in the flask, 0.6 g (2.1 mmols) of the intermediate (1) prepared in Referential Example 1 was added. Further, 4.89 dm³ (volume at 25° C., 0.2 mol reduced as HF) of hydrofluoric acid was introduced as gradually blown in the resultant solution, continuously stirred at 0° C. for two hours and then made to add 66 g of dichloromethane.

The resultant mixture was distilled to expel the reaction solvent by evaporation and the residue of the distillation was passed through a basic alumina column. When the effluent from the column was analyzed by the GC-MS, it was confirmed to contain therein 4-difluoromethyl benzaldehyde (product 1) and 1,4-bis-(difluoromethyl)benzene (product 2). In the GC analysis which was separately performed, the area ratio of product 1/product 2 was found to be 30/70.

EXAMPLE 9

A three-neck flask, 200 ml in inner volume, made of glass and provided with a stirrer was charged with 50 mL dichloromethane (DCM) and 36 g N-bromosuccinimide (NBS) and, after having the interior thereof displaced with argon gas (moisture content of not more than 1 volppm), further charged with 2.4 mL pyridine hydrogen fluoride (produced by Aldrich Corp.; the weight ratio of HF to pyridine: 7 to 3; density 1.2; abbreviated as "HF-Pyr" in Table 2 below). The mixture in the three-neck flask, with the flask placed in ice water, was made to add 7.4 g (25.9 mmols) of the intermediate (4) synthesized in Referential Example 4 as kept continuously stirred at an inner temperature of 0° to 5° C. The amount of NBS was about two equivalences to the amount of intermediate (4). It was further stirred continuously at the temperature of ice for two hours.

To the resultant reaction mixture, an aqueous 20% sodium hydroxide solution was added until the pH value of the water phase rose above 10. The precipitate which was generated during the course of the neutralization was separated by filtration. The organic layer of the filtrate was washed with dilute hydrochloric acid and then distilled under a reduced pressure (50 mmHg, 93° to 99° C.), to isolate 1,4-bis (difluoromethyl)benzene.

EXAMPLES 10 to 19

Isolation of 1, 4-bis (difluoromethyl)benzene was performed by following the procedure of Example 9 while changing the amounts of relevant reactants as shown in the following table. In Examples 16 and 17, 1,3-dibromo-5,5-dimethyl hydantoin (DMH) was used as a bromine-containing compound in place of N-bromosuccinimide (NBS). In Examples 16 and 17, a three-neck flask having an inner volume of 1 liter was used in place of the three-neck flack having the inner volume of 200 ml. In Example 19, the use of a bromine-containing compound was omitted.

The compositions of Examples 9 to 19 and the results obtained therefor are shown in Table 2 below. Unexpectedly, the yields in Examples 12 and 13 were 100%, i.e., no by-products were formed in these examples.

TABLE 2

| | DCM (ml) | NBS (g) | HF-Pyr (ml) | Intermediate (4) | Yield |
|---|---|---|---|---|---|
| Example 9 | 50 | 36 | 2.4 | 7.4 | 6 |
| Example 10 | 50 | 36 | 6.1 | 7.4 | 18.8 |
| Example 11 | 50 | 36 | 9.7 | 7.4 | 39.0 |
| Example 12 | 50 | 36 | 12.1 | 7.4 | 100 |
| Example 13 | 50 | 36 | 24.2 | 7.4 | 100 |
| Example 14 | 50 | 18 | 24.2 | 7.4 | 40.8 |
| Example 15 | 50 | 9 | 24.2 | 7.4 | 21.0 |
| Example 16 | 300 | DMH; 17.4 | 14.5 | 4.44 | 30 |
| Example 17 | 300 | DMH; 174 | 145 | 44.4 | 30 |
| Example 18 | 50 | 3.6 | 2.4 | 0.74 | 32 |
| Example 19 | 50 | —* | 12.0 | 7.4 | 20 |

*No bromine-containing compound used.

The entire disclosure of Japanese Patent Application No. 10 –9135 filed on Jan. 20, 1998 including specification, claims, drawings and summary are incorporated herein by reference in its entirety.

What is claimed is:

1. A process for the production of 1,4-bis(difluoroalkyl) benzene derivative of the formula:

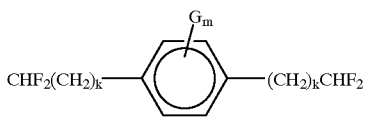

where k is 0, G stands for a halogen group, and m is 0, which process comprises reacting compound (A) selected from the group consisting of:

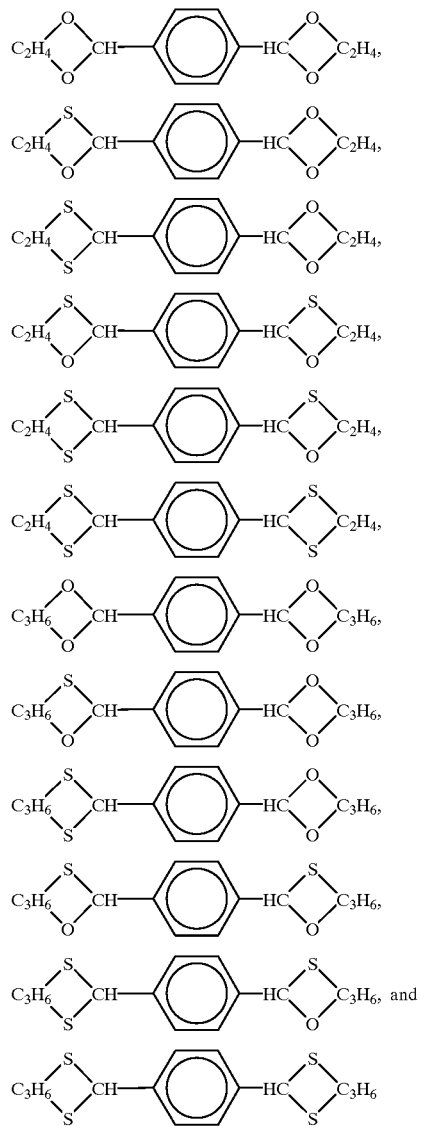

with a fluoride-containing species, the molar ratio of the fluorine-containing species to compound (A) being in the range of 20–40, in the presence of a bromine-containing compound, which is in an amount of 2 to 3 equivalences to the amount of compound (A), in an organic solvent at −80° C. to 30° C., the final concentration of compound (A) being in the range of 3 to 30% by weight.

2. The process of claim 1, wherein the reaction temperature is 0° C. and compound (A) is

3. The process of claim 1, wherein the reaction temperature is 0° C. to 5° C. and compound (A) is
4. The process of claim 1, wherein the reaction temperature is 0° C. to 5° C.
* * * * *